United States Patent [19]

Hurme

[11] Patent Number: 5,478,487
[45] Date of Patent: Dec. 26, 1995

[54] METHOD FOR DENATURING ROAD SALT AND DENATURED ROAD SALT

[75] Inventor: Taisto T. Hurme, Turku, Finland

[73] Assignee: Hurme Consulting Oy, Turku, Finland

[21] Appl. No.: 373,302

[22] PCT Filed: Jul. 16, 1993

[86] PCT No.: PCT/FI93/00300

§ 371 Date: Jan. 17, 1995

§ 102(e) Date: Jan. 17, 1995

[87] PCT Pub. No.: WO94/02558

PCT Pub. Date: Feb. 3, 1994

[30]  Foreign Application Priority Data

Jul. 28, 1992  [FI]  Finland ..................... 923407

[51] Int. Cl.⁶ ........................................ C09K 3/18
[52] U.S. Cl. ............................. 252/70; 106/13
[58] Field of Search ............... 106/13; 252/70; 548/210

[56]  References Cited

U.S. PATENT DOCUMENTS

| | | | |
|---|---|---|---|
| 3,350,315 | 10/1967 | Schneider | 252/70 |
| 3,833,504 | 9/1974 | Neitzel et al. | 252/70 |
| 4,064,316 | 12/1977 | Curtis | 428/522 |
| 4,430,240 | 2/1984 | Sandvig et al. | 106/13 |
| 4,434,190 | 2/1984 | Dubois et al. | 252/70 |
| 4,661,504 | 4/1987 | Hollander et al. | 514/373 |
| 4,824,588 | 4/1989 | Lin | 252/70 |
| 4,960,531 | 10/1990 | Connor et al. | 106/13 |
| 5,366,650 | 11/1994 | Wiesenfeld et al. | 106/13 |
| 5,376,293 | 12/1994 | Johnston | 106/13 |

FOREIGN PATENT DOCUMENTS

| | | |
|---|---|---|
| 0010574 | 5/1980 | European Pat. Off. . |
| 2847350 | 5/1980 | Germany . |

OTHER PUBLICATIONS

Sugden et al., "Determination of Denaturants in Alcoholic Toilet Preparations", Analyst, 103:653–656 (Jun. 1978).
Lahdem, Römpp Chemie Lexicon, 1:1373 (1966, no month cited in copy of article).
Römpp Chemie Lexicon, vol. 1, p. 1373 (1966) with English language translation no month.
Soveri, Kemia–Kemi, 19, pp. 117–119 (1992) with English language Abstract no month.

Primary Examiner—Anthony Green
Attorney, Agent, or Firm—Merchant & Gould; Smith, Edell, Welter & Schmidt

[57]  ABSTRACT

The invention relates to a method for denaturing road salt by adding an aversive agent, such as benzyldiethyl-(2.6-xylylcarbamoyl-methyl) ammonium benzoate, i.e. denatonium benzoate, or N,N,N,N-benzyldiethyl-(2,6-xylylcarbamoyl-methyl)ammonium saccharine, i.e. denatonium saccharine, or brucine, or a derivative of these, to the road salt either before applying the road salt or afterwards on the road salt by atomizing or spraying.

13 Claims, No Drawings

METHOD FOR DENATURING ROAD SALT AND DENATURED ROAD SALT

The invention relates to a method for denaturing road salt by adding benzyldiethyl-(2,6-xylylcarbamoyl-methyl)ammonium benzoate, i.e. denatonium benzoate, or N,N,N,N-benzyldiethyl-(2,6-xylylcarbamoyl-methyl)ammonium saccharine, i.e. denatonium saccharine, or brucine, or a derivative of these, to the road salt either before applying the road salt or afterwards on the road salt by atomizing or spraying. Said substance is used in an amount of 0.1 to 500 ppm based on the weight of the road salt. The invention also relates to a road salt containing said substance. The road salt according to the invention preferably contains 0.5 to 100 ppm benzyldiethyl-(2,6-xylylcarbamoyl-methyl)ammonium benzoate, i.e. denatonium benzoate, or a corresponding derivative, Or 0.1 to 50 ppm N,N,N,N-benzyldiethyl-( 2,6-xylylcarbamoyl-methyl)ammoniumsaccharine, i.e. denatonium saccharine, or a corresponding derivative.

It has been found that animals do not eat or touch the road salt according to the invention. Hence it is possible to improve road safety and to totally avoid, for example, collisions with reindeer or elks on sections of the road on which denatured road salt is being used.

Very many animals, domestic animals and wild forest animals included, have a tendency to eat the compounds used in salting roads. Road salt usually contains mainly conventional sodium chloride, but also other inorganic compounds which have been added on purpose to the road salt or which are inherently contained in it depending on from what kind of source the road salt is made, for example, rock salt or marine salt. The road salt may also contain various kinds of calcium compounds, such as calcium chloride, which is used as such, for example, to bind the dust on sand roads. Besides calcium chloride the road salts contain e.g. magnesium oxide and magnesium chloride, and in some cases also calcium acetate and magnesium acetate as described in numerous patents relating to the manufacture of road salt (e.g. U.S. Pat. No. 3,833,504, U.S. Pat. No. 3,350,315 and GB 164622).

Road salt may also contain organic additives the purpose of which is to make the salt stick to the road surface so that it will not be transported away from the road and later into the groundwater, for instance. Such compounds are e.g. copolymers of polystyrene and polybutadiene. A compound like this is described in, for example, U.S. Pat. No. 4,434, 190.

Corrosion preventing compounds, such as calcium cyanamide, can also be added to the road salt (DE 2847350 and EP 10574).

The inventions according to said patents are characterized in that the compounds mentioned and the production methods of the road salt or the additives aim at something else than preventing animals from utilizing the road salt. None of said patents discloses that the additives mentioned would have such an effect that animals would no longer like to eat road salt. Said patents are silent about the problem of how to prevent animals from eating road salt and thereby to improve road safety.

A central feature of the present invention is that by using the mentioned very effective aversive agents the amounts needed are very small compared with other possible repellent compounds that can be added to the road salt or onto the road. It is surprising that already a very small amount of aversive agent is enough to make the road salt unpleasant for animals. The use of said aversive agents in accordance with the present invention for denaturing road salt has a superior economic advantage as compared with, for example, other chemical compounds. Road salts are produced from cheap raw materials and therefore it is necessary to avoid high additive costs.

The use of aversive agents according to the invention has the further advantage that the properties of the road salt used are not changed in any way since the proportion of the necessary aversive agents, based on the total weight of the road salt, is extremely small. Thus the application of the denatured road salt is as easy as the application of normal road salt since the aversive agents do not change the physico-chemical parameters of the road salt. The aversive agents are also inert to the effects of anti-caking substances and additives used in the binding of road salt. The dosage of aversive agents into the road salt during its production or afterwards by spreading on the road does not require any special equipment, which makes these substances very suitable for use in industrial production and for large-scale application.

Yet another advantage of the use of aversive agents according to the invention is that the water in wells lying too close to the road receives a discernible bad taste, i.e. it will not be used as drinking water any longer. A similar effect can be expected in berries and mushrooms which are picked too close to the road. Additionally, this gives a forewarning of excessive use of road salt. As is known, salting of roads affects the quality of the groundwater, which is probably the most pronounced negative effect that the use of road salt has on the environment (cf. Soveri, J., Kemia-Kemi, Vol 19 (1992)2, pages 117–119).

The invention is not restricted to the embodiment disclosed in the description, but it can be varied within the scope of the enclosed claims in order to achieve denaturing of road salt. The invention will be described in greater detail in the following examples.

EXAMPLE 1

20 g of an aversive agent were carefully mixed into 5,000 kg of rock salt, the chemical name of the aversive agent being benzyldiethyl(2,6-xylylcarbamoylmethyl)ammonium benzoate. The substance is known under the commercial name Bitrex and the trivial name denatonium benzoate. In order to ensure homogeneity the mixing was carried out so that said amount of said aversive agent was first mixed in a cone mixer with 2 kg of rock salt, which first premix was then added in a horizontal mixer to 250 kg of rock salt. The resulting second premix was mixed in a third horizontal mixer to the final concentration, i.e. 4 ppm (mixing ratio 1:250,000).

The resulting denatured road salt was spread with normal equipment used for salting roads on such a section of the road where reindeer used to come every day to eat the road salt. After the salt had been spread a 24 hour watch was arranged for that section of the road in such a manner that the normal behaviour of the reindeer was not disturbed. In the beginning the reindeer came to that section of the road to eat salt as they had used to do, but after having tasted the denatured road salt once they left that section of the road. According to the observations the reindeer did not come back again to eat at the same place, which means that the same reindeer did not come back to the denatured section of the road.

EXAMPLE 2

Conventional road salt had been spread in a normal manner on a section of the road. The salt attracted reindeer to eat it. Three hours after the spreading of the salt, new road salt was spread on the salt, said new salt containing a bitter tasting denaturing agent which had been mixed homogeneously with the road salt in the manner described in example 1.

The aversive agent used was N,N,N,N-benzyldiethyl-(2,6-xylylcarbamoyl-methyl)ammonium saccharine which is also called denatonium saccharine. The final concentration of the substance was 1 ppm.

When the denatured road salt had been spread on the old road salt the reindeer came back to taste the salt, but left immediately after having tasted it once and did not return to the same section of the road.

EXAMPLE 3

Wet road salt was prepared in a normal manner with the exception that brucine sulphate had in advance been dissolved in the water to be used, the brucine sulphate being a water-soluble derivative of the known aversive agent brucine. The concentration of brucine by weight of the salt was 100 ppm (mixing ratio 1:10,000).

Wet denatured road salt like this was spread by known wet salting equipment on a section of a road which was known as a place where elks used to come to eat salt and thereafter cross the road. Road salt prepared in the same manner was also spread on a section of a road which was known as a place where reindeer used to come to eat salt. During a long-term monitoring of said road portions, which lasted a month and was carried out by means of a counter based on a light cell, the number of animals crossing the road was reduced to one tenth of the number before the introduction of the denatured road salt. When the road was again salted with normal road salt the number of animals crossing the road slowly increased during a period of two months almost to the old level. On the basis of this it was concluded that the change of the salt on the road had led to a change in the number of animals crossing the road.

EXAMPLE 4

An exactly weighed portion of 20 kg of road salt prepared in the manner according to example 1 was placed in a feeding place for elks in a shelter where it was protected from the rain and wind. For the sake of comparison, the same amount of normal undenatured road salt was placed on the other side of a separating wall in the same shelter. After three weeks the salt amounts were controlled. The denatured salt had been touched, but less than 5 percent of it had vanished in one way or another. The undenatured salt had almost completely vanished. Since the surrounding conditions were the same for both salts, the only reason for this kind of test result was the different taste of the salts.

EXAMPLE 5

On a section of the road on which conventional road salt had been spread, reindeer expectedly gathered to eat salt. When this was observed a concentrated aqueous solution of denatonium saccharine was sprayed from a tank lorry as a fine spray in such an amount that it was estimated that the amount of aversive agent sprayed on the road salt amounted to almost the same as if the mixing ratio had been 1:500,000. When the aversive agent had been sprayed on the road the reindeer came back to the road, but left in a hurry after having tasted only once the road salt treated in this manner.

I claim:

1. A method for denaturing road salt comprising adding to the road salt an aversive agent which includes benzyldiethyl-(2,6-xylylcarbamoylmethyl)ammonium benzoate, N,N,N,N-benzyldiethyl-(2,6-xylylcarbamoylmethyl)ammonium saccharine, brucine, or a derivative thereof.

2. The method of claim 1 wherein adding the aversive agent comprises applying the aversive agent to road salt spread on a road.

3. The method of claim 1 wherein adding the aversive agent comprises mixing the aversive agent with the road salt before applying the road salt.

4. The method of claim 1 comprising adding 0.1 to 500 ppm (based on the weight of the road salt) of the aversive agent to the road salt.

5. The method of claim 1 wherein the road salt includes rock salt or marine salt.

6. The method of claim 1 wherein the road salt includes sodium chloride, calcium chloride, calcium acetate, magnesium chloride, magnesium acetate or magnesium oxide.

7. The method of claim 1 wherein the aversive agent includes benzyldiethyl-(2,6-xylylcarbamoylmethyl)ammonium benzoate, N,N,N,N-benzyldiethyl-(2,6-xylylcarbamoylmethyl)ammonium saccharine, or brucine sulfate.

8. A denatured road salt composition comprising:

a road salt component; and 0.1 to 500 ppm of an aversive agent which includes benzyldiethyl-(2,6-xylylcarbamoylmethyl)ammonium benzoate, N,N,N,N-benzyldiethyl-(2,6-xylylcarbamoylmethyl)ammonium saccharine, brucine, or a derivative thereof.

9. The composition of claim 8 comprising 0.5 to 100 ppm benzyldiethyl-(2,6-xylylcarbamoylmethyl)ammonium benzoate.

10. The composition of claim 8 comprising 0.1 to 50 ppm N,N,N,N-benzyldiethyl-(2,6-xylylcarbamoylmethyl)ammonium saccharine.

11. The composition of claim 8 wherein the road salt component includes rock salt or marine salt.

12. The composition of claim 8 wherein the road salt component includes sodium chloride, calcium chloride, calcium acetate, magnesium chloride, magnesium acetate or magnesium oxide.

13. The composition of claim 8 wherein the aversive agent includes benzyldiethyl-(2,6-xylylcarbamoylmethyl)-ammonium benzoate, N,N,N,N-benzyldiethyl-(2,6-xylylcarbamoylmethyl)ammonium saccharine, or brucine sulfate.

* * * * *